(12) United States Patent
Barat et al.

(10) Patent No.: US 8,043,830 B2
(45) Date of Patent: Oct. 25, 2011

(54) BIOTIN-LIGASE SYSTEM FOR SECRETION OF BIOTINYLATED PROTEIN

(75) Inventors: Bhaswati Barat, Los Angeles, CA (US); Anna M. Wu, Sherman Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/363,678

(22) Filed: Jan. 30, 2009

(65) Prior Publication Data

US 2009/0275081 A1 Nov. 5, 2009

Related U.S. Application Data

(60) Provisional application No. 61/025,656, filed on Feb. 1, 2008.

(51) Int. Cl.
*C12P 21/00* (2006.01)
*C12P 21/04* (2006.01)

(52) U.S. Cl. .................. 435/69.1; 435/69.7

(58) Field of Classification Search .......... None
See application file for complete search history.

(56) References Cited

U.S. PATENT DOCUMENTS

| | | | | |
|---|---|---|---|---|
| 6,903,203 B2 * | 6/2005 | Copley et al. | ............... | 536/23.53 |
| 2002/0142355 A1 * | 10/2002 | Barry et al. | ............... | 435/7.5 |

FOREIGN PATENT DOCUMENTS

| WO | WO 00/05406 | * | 2/2000 |
|---|---|---|---|

OTHER PUBLICATIONS

Yazaki et al. Mammalian expression and hollow fiber bioreactor production of recombinant anti-CEA diabody and minibody for clinical application. J. Immunological Method (2001) 253, 195-208.*
Barat, B. et al., "Metabolic biotinylation of recombinant antibody by biotin ligase retained in the endoplasmic reticulum," *Biomolecular Engineering*, 2007, vol. 24, pp. 283-291.
Nesbeth, D. et al., "Metabolic Biotinylation of Lentiviral Pseudotypes for Scalable Paramagnetic Microparticle-Dependent Manipulation," *Molecular Therapy*, Apr. 2006, vol. 13, No. 4, pp. 814-822.
Parrott, M.B. et al., "Metabolic Biotinylation of Recombinant Proteins in Mammalian Cells and in Mice," *Molecular Therapy*, Jan. 2000, vol. 1, No. 1, pp. 96-104.
Parrott, M.B. et al., "Metabolic Biotinylation of Secreted and Cell Surface Proteins from Mammalian Cells," *Biochemical and Biophysical Research Communications*, 2001, vol. 281, No. 4, pp. 993-1000.
Verhaegen, M. et al., "Recombinant *Gaussia* Luciferase. Overexpression, Purification, and Analytical Application of a Bioluminescent Reporter for DNA Hybridization," *Analytical Chemistry*, Sep. 1, 2002, vol. 74, No. 17, pp. 4378-4385.

* cited by examiner

*Primary Examiner* — Nashaat Nashed
(74) *Attorney, Agent, or Firm* — Morgan, Lewis & Bockius LLP; Annette S. Parent

(57) ABSTRACT

The present invention provides methods of metabolically biotinylating recombinant proteins. Cell lines and specific protein and nucleic acid constructs for use in the methods of the present invention are also provided herein.

15 Claims, 10 Drawing Sheets

Figure 1

(A)  Parental Db:    V$_L$-GGGSGGGG-V$_H$

1. Db-BD123    V$_L$-GGGSGGGG-V$_H$-GSTS-[ BD123 ]

2. Db-BP15     V$_L$-GGGSGGGG-V$_H$-GSTSGS<u>GLNDIFEAQKIEWHE</u>

3. Db-BP15-His V$_L$-GGGSGGGG-V$_H$-GSTSGS<u>GLNDIFEAQKIEWHE</u>HHHHHH

4. Db-His-BP15 V$_L$-GGGSGGGG-V$_H$-GSTSHHHHHHGAAG<u>GLNDIFEAQKIEWHE</u>

(B)  [ BirA ]—DYKD

[ BirA ]—DYKDEL

BIOTIN-LIGASE SYSTEM FOR SECRETION OF BIOTINYLATED PROTEIN

STATEMENT AS TO RIGHTS TO INVENTIONS MADE UNDER FEDERALLY SPONSORED RESEARCH OR DEVELOPMENT

This invention was made with Government support of Grant No. CA086309 and CA119367, awarded by the National Institute of Health. The Government has certain rights in this invention.

CROSS-REFERENCES TO RELATED APPLICATIONS

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Biotin (vitamin H), an essential coenzyme required by all forms of life, is only synthesized by plants, most bacteria and some fungi. In living cells, a few metabolic enzymes are naturally biotinylated through post-translational modification that is carried out by an intracellular enzyme, biotin protein ligase (BPL), also known as holocarboxylase synthetase [EC 6.3.4.10]. BPL catalyzes the formation of an amide linkage between the carboxyl group of biotin and the ε-amino group of a specific lysine residue of the substrate protein in a two-step reaction ([Cronan, 1990] and [Wood and Barden, 1997]). The non-covalent interaction between avidin/streptavidin and biotin represents one of the strongest and most specific interactions amongst biological molecules ($K_D=10^{-14}$ to $10^{-15}$ M). This property has been exploited by researchers who have attached biotin 'tags' to proteins for easy detection, labeling, immobilization and purification ([Cull and Schatz, 2000], [Kumar and Snyder, 2002], [de Boer et al., 2003], [Kojima et al., 2006] and [Krepkiy et al., 2006]). Biotin labeling has also been applied to drug targeting ([Ohno et al., 1996] and [Asai et al., 2005]) and viral gene therapy vector-targeting strategies ([Smith et al., 1999], [Parrott et al., 2003], [Campos and Barry, 2004] and [Arnold et al., 2006]).

Biotin labeling of drugs, proteins or virus has traditionally been performed in vitro by chemical methods, where an activated biotin derivative is conjugated to protein surface residues (commonly lysines) or carbohydrate moieties ([Bayer and Wilchek, 1990], [Diamandis and Christopoulos, 1991], [Ohno et al., 1996] and [Smith et al., 1999]). However, these methods result in random and heterogeneous modification, which can lead to the inactivation of biological function and cross-linking or aggregation after mixing with streptavidin or avidin. Antibody biotinylation by chemical methods generally leads to the preparation of heterogeneous conjugates. Furthermore, biotinylation of the residues in the binding site of antibodies can alter their binding properties (Saviranta et al., 1998) and result in loss of affinity.

An alternative approach to chemical methods was first demonstrated by Cronan (1990). Fusion of the biotin attachment sites of proteins from four different species to the carboxyl terminus of β-galactosidase enabled biotinylation in *Escherichia coli* by endogenous biotin ligase. The functional interaction between biotin ligases and their protein substrates shows a very high degree of conservation throughout evolution, since biotinylation occurs even with enzymes and substrates from widely divergent species (Chapman-Smith and Cronan, 1999). The most studied endogenous biotinylated protein is the 1.3S subunit of the transcarboxylase domain of *Propionibacterium shermanii* (PSTCD), which is structurally very similar to that of *E. coli* acetyl-CoA carboxylase (Reddy et al., 1998). By fusing the biotin acceptor peptide domain of PSTCD to the target protein, it was demonstrated that biotinylation could occur in bacterial, yeast, insect and mammalian cells ([Smith et al., 1999], [Parrott and Barry, 2001] and [Verhaegen and Christopoulos, 2002]). A recent in vivo imaging study showed that tumor cells expressing PSTCD tagged surface receptor protein was detected using a variety of imaging agents coupled to streptavidin (Tannous et al., 2006). Biotinylation can occur either by cellular endogenous protein-biotin ligase or by the coexpression of an exogenous biotin ligase, in most cases that of bacterial BirA enzyme (Tsao et al., 1996).

Smaller peptide tags (<23 aa) identified by peptide libraries were also found to be biotinylated in vitro with kinetics comparable to those of natural biotin acceptor sequence (Schatz, 1993). A 15 residue peptide (GLNDIFEAQKIEWHE (SEQ ID NO:1), Biotin AviTag™) (Beckett et al., 1999) with 100% biotinylation efficiency was used for specific biotinylation of fusion protein in *E. coli*, insect and mammalian cells ([Smith et al., 1998], [Wu et al., 2002], [de Boer et al., 2003], [Viens et al., 2004], [Yang et al., 2004], [Warren et al., 2005] and [Tirat et al., 2006]). Utilizing this small peptide in vivo biotinylation has also been performed on the surface of yeast (Parthasarathy et al., 2005).

Antibodies can be engineered into a variety of formats that retain binding specificity and exhibit optimal properties for in vitro or in vivo applications. Single-chain antibody fragments (scFvs), produced by genetically fusing variable light ($V_L$) and heavy ($V_H$) chain domains of a parental antibody through a peptide linker, represent the smallest functional unit (25-30 kDa) that still retains the capacity to bind antigen. Production of single-chain antibody scFv dimers (also known as diabodies, 55 kDa) can be forced by shortening the peptide linker, which in turn enhances the binding activity (Holliger et al., 1993).

Despite recent advances in the chemical and metabolic methods of producing biotinylated polypeptides, there remains a need in the art for highly specific and highly efficient methods of producing large quantities of biotinylated polypeptides for applications such as medical diagnostics and pharmaceutical administration. The present invention fulfills these and other need by providing novel methods, cell lines, systems, and kits for efficient metabolic biotinylation of secreted polypeptides.

BRIEF SUMMARY OF THE INVENTION

The present invention provides two methods for biotinylation of proteins secreted from eukaryotic cells. In one system, the biotin ligase is co-secreted from cells along with substrate protein enabling extracellular biotinylation of the tagged protein. In the other system, biotin protein ligase (e.g., biotin protein ligase (BPL), also known as holocarboxylase synthetase [EC 6.3.4.101]) is engineered to be retained in the endoplasmic reticulum (ER) and metabolically biotinylates the secretory protein as is passes through the ER. Utilization of ER retained biotin protein ligase for biotinylation of proteins is an attractive alternative for efficiently producing uniformly biotinylated proteins and polypeptides for a variety of avidin/streptavidin-biotin technologies.

In one aspect, the invention provides uniformly biotinylated proteins and polypeptides. In another aspect, the invention provides biotin ligases that are engineered to be retained in the ER of eukaryotic cells. Transfection of eukaryotic cells with vectors containing the chimeric ligases provides cells which express the biotin ligase enzyme in the ER. As such, heterologous secretory proteins that contain biotinylation acceptor sequences will then be efficiently biotinylated as they pass through the ER.

The methods and compositions according to the invention can be used to attach biotin 'tags' or moieties to targeted proteins for easy detection, labeling, immobilization, purification, targeting, and the like. The biotinylated proteins can be used in pharmaceutical administration, drug targeting, and other applications of avidin/streptavidin-biotin technologies.

In one aspect, the present invention provides novel methods of producing biotinylated proteins. In one embodiment, these methods comprise the metabolic biotinylation of proteins secreted from eukaryotic cells. In certain embodiments, the methods of the invention comprise expressing a heterologous target polypeptide having a biotinylation acceptor sequence in a eukaryotic cell that has been engineered to express an exogenous biotin ligase enzyme.

In certain embodiments, the methods of the invention comprise the co-secretion of a target heterologous protein and an exogenous biotin protein ligase. In other embodiments, the methods comprise the expression of an exogenous biotin protein ligase that has been engineered to be retained in the endoplasmic reticulum (ER).

In another aspect of the invention, heterologous biotin protein ligases are provided. In certain embodiments, the heterologous biotin protein ligases of the invention have been engineered to be retained in the ER.

In one aspect of the invention, cell lines for the production of uniformly biotinylated polypeptides are provided. In certain embodiments of the invention, the cell lines provided express an exogenous biotin ligase that functions to biotinylate target polypeptides having an engineered biotinylation acceptor sequence. Generally, the cell lines of the invention are useful for producing heterologous target proteins that have been biotinylated with high specificity and high efficiency.

In yet another aspect, the present invention provides kits for producing biotinylated polypeptides. The kits of the invention may include cell lines provided herein, heterologous biotin protein ligases of the invention, vectors for the expression of target polypeptides, and the like.

BRIEF DESCRIPTION OF THE DRAWINGS

FIG. 1. Schematic presentation of the fusion proteins. (A) Anti-CEA diabody fusion proteins. T84.66 $V_L$ and $V_H$ are joined by an 8 aa linker, to form the diabody. 1-4, diabody variants with 123 aa biotin acceptor domain (BD123) or 15 aa peptide (BP15) at the C-terminus. A 4 aa (GSTS) (SEQ ID NO:17) or a 6 aa (GSTSGS) (SEQ ID NO:18) linker was used between Db and biotin acceptor substrate. (B) Biotin protein ligase (BirA). The amino acids DYKD (SEQ ID NO:11) and DYKDEL (SEQ ID NO:12) at the C-terminus are for secreted and ER-retained biotin ligase, respectively. The heavy and light chains are conjugated with the linker sequence GGGSGGGG (SEQ ID NO: 19). GSTSGSGLNDIFEAQKIEWHE (SEQ ID NO:20) is a biotinylation acceptor sequence and linker fused to the parental Db. GSTSGSGLNDIFEAQKIEWHEHHHHHH (SEQ ID NO:21) is a biotinylation acceptor sequence, linker, and hexa-histidine tag fused to the parental Db, as is GSTSHHHHHHGAAGGLNDIFEAQKIEWHE (SEQ ID NO:22).

DETAILED DESCRIPTION OF THE INVENTION

Figure 2:
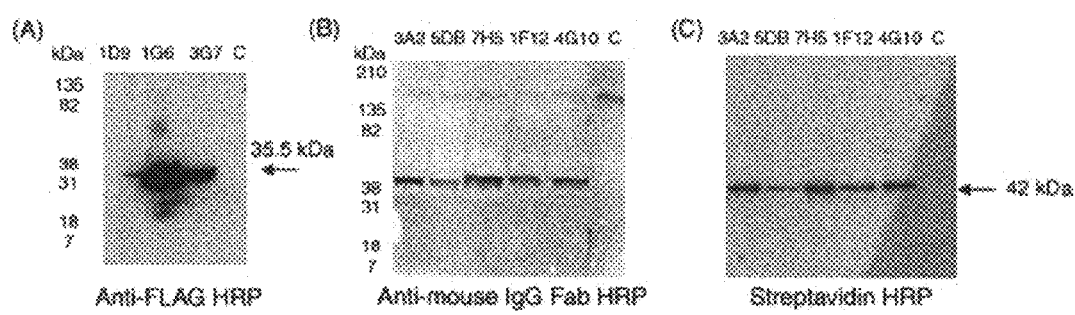
FIG. 2. Western blots of Db-BD123 fusion protein co-secreted with biotin ligase (BirA-DYKD) (SEQ ID NO:13). (A) Expression of secreted BirA-DYKD (SEQ ID NO:13) was detected with anti-FLAG M2 antibody. (B) Expression of Db-BD123 in different clones was detected with HRP-conjugated anti-mouse Fab. (C) Same Db-BD123 expressing clones detected with SA HRP. The molecular weight standard is indicated. C, control, non-transfected NS0 cells.

Due to its strength and specificity, the interaction between avidin and biotin has been used in a variety of scientific and medical applications ranging from immunohistochemistry to drug targeting. The present invention provides methods for the biotinylation and large-scale production of polypeptides secreted from eukaryotic cells. In certain embodiments of the invention, the methods and cells of the invention rely on the expression of a heterologous biotin protein ligase. In a specific embodiment, the ligase is the *Escherichia coli* biotin protein ligase BirA.

In one system provided by the present invention, an exogenous biotin ligase may be co-secreted from the cells along with substrate protein enabling extracellular biotinylation of the tagged protein. In a second system provided by the present invention, as exogenous biotin ligase that has been engineered to be retained in the endoplasmic reticulum (ER) is used to metabolically biotinylates the secretory protein as it passes through the ER.

As a demonstration of the methods provided by the present invention, the examples describe a line of experimentation wherein an engineered antibody fragment, a diabody with specificity for carcinoembryonic antigen (CEA), was fused to the biotin acceptor domain (123 amino acid) of *Propionibacterium shermanii*. Coexpression of the fusion protein with ER retained biotin ligase showed higher biotinylation efficiency than biotinylation by co-secreted ligase. Biotinylation of the anti-CEA diabody tagged with a short (15 amino acid, Biotin Avitag™) biotin acceptor peptide was also successful. Utilization of ER retained biotin ligase for biotinylation of protein is an attractive alternative for efficiently producing uniformly biotinylated heterologous proteins for a variety of avidin-biotin technologies.

We have previously described an engineered anti-carcinoembryonic antigen (CEA) diabody (Db), constructed from the variable regions of the murine anti-CEA monoclonal antibody T84.66 (Wu et al., 1999). Attempts to biotinylate the anti-CEA diabody by chemical methods resulted in inactivation and finally precipitation of the protein when mixed with streptavidin. To circumvent this problem, we developed a fusion protein comprised of the anti-CEA diabody and the 123 aa biotin acceptor domain from *P. shermanii* (referred to here as BD123) to generate Db-BD123. The fusion protein was coexpressed in mammalian cells with BirA, the BPL of *E. coli*. Secreted and ER-retained forms of BPL were developed, and the efficiency of biotinylation of Db-BD123 was higher using ER-retained ligase compared to secreted ligase. BD123 was replaced by a 15 amino acid short biotin acceptor peptide (defined here as BP15) to produce Db-BP15. Biotinylation efficiency of the fusion protein by ER-retained BPL was higher using BP15 compared to BD123. This technology allows metabolic biotinylation of secreted proteins eliminating the need to purify and treat with exogenous reagents. This method is a useful approach for efficiently producing uniformly biotinylated proteins.

The present invention provides novel systems and methods for the metabolic biotinylation of fusion proteins in eukaryotic cells. Initial studies demonstrate that the Db-BD123 fusion protein was biotinylated by both versions of biotin ligase (secreted and ER-retained). In additional three variants of the anti-CEA Db with BP15 were also efficiently biotinylated in presence of ER-retained ligase. Biochemical and biological characterization show that the fusion proteins assembled into the expected molecular weight fragments and bound antigen effectively.

Traditional in vitro enzymatic biotinylation is conducted on purified proteins and requires many steps including concentration of protein, buffer exchange for optimal enzymatic activity, enzymatic biotinylation at room temperature, and buffer exchange for removal of free biotin from enzymatic reaction (Altman et al., 1996). In contrast, the present invention provides for the metabolic biotinylation of protein in vivo by biotin ligase, which shortens and streamlines a lengthy process and reduces the chance of protein degradation during biotinylation by exogenous biotin ligase.

Successful development of biotinylated recombinant antibody fragments required three components: the antibody, the biotin acceptor domain and the linker between the two. The anti-CEA diabody (non-covalent scFv dimer) used to demonstrate the novel methods of the present invention was chosen as the minimal, bivalent-engineered antibody fragment that is still capable of efficient localization to CEA-expressing tumors in vivo (Wu et al., 1999). Furthermore, from the X-ray crystallographic structure of anti-CEA Db it was found that C-termini of the diabody subunits are almost 70 Å apart and on an alternate face from the antigen-combining site (Carmichael et al., 2003). Thus, fusion of an additional partner domain to the C-termini of the diabody should not interfere with the antigen binding.

Figure 9:
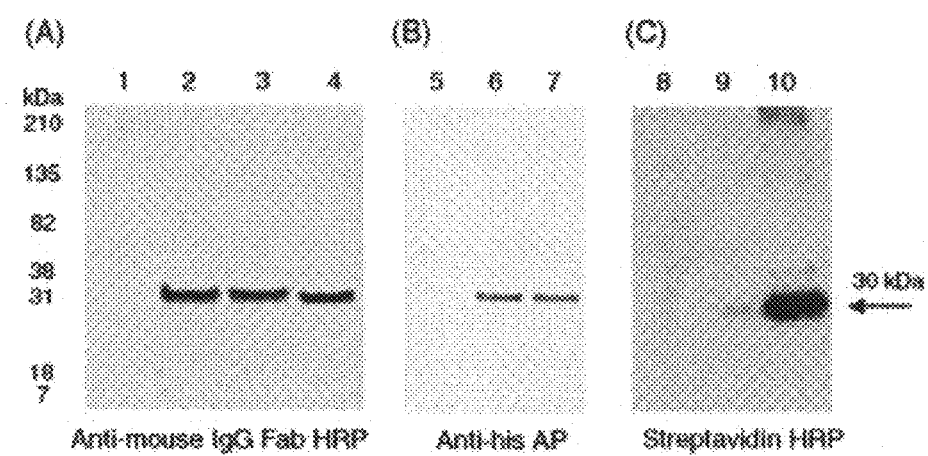
FIG. 9. Western blots of media supernatants expressing Db-BP15-His in absence of BirA. (A) Expression of diabody was detected with anti-Fab antibody. Lane 1, non-transfected NS0 cells (negative control); lanes 2 and 3, cell lines expressing Db-BP15-His in absence of BirA; lane 4, cell line expressing Db-BP 15-His in presence of BirA (positive control). (B) Detection of 6×His (SEQ ID NO:24) tag using AP-conjugated anti-His antibody. Lane 5, non-transfected NS0 cells (negative control); lanes 6 and 7, cell lines expressing Db-BP15-His in absence of BirA. (C) Detection of biotin using SA HRP. Lanes 8 and 9, cell lines expressing Db-BP15-His in absence of BirA; lane 10, cell line expressing Db-BP15-His in presence of BirA (positive control).
Figure 10:
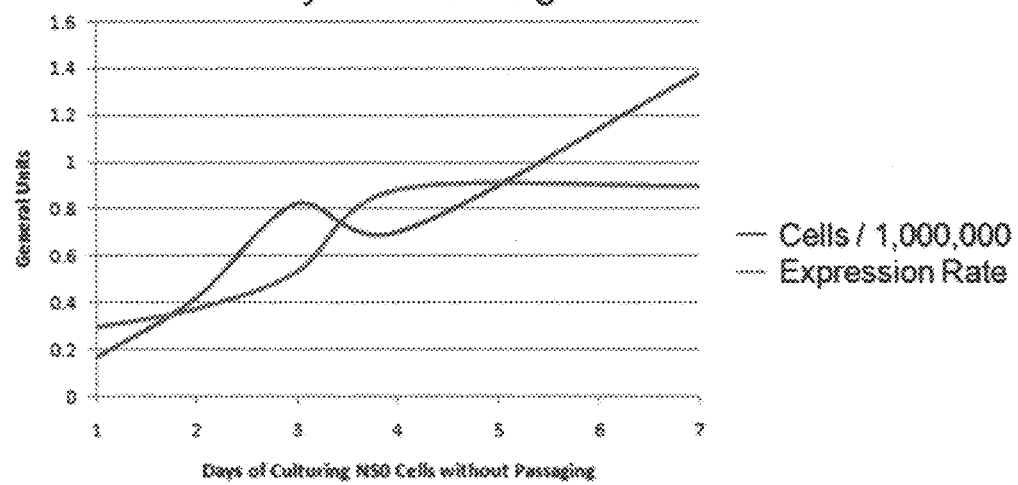
FIG. 10. Expression rate of Anti-CEA biotinylated diabody secreted from NS0 cells over the period of a week in the absence of passaging.

Initially the large biotinylation tag (123 aa) derived from the biotin acceptor domain present in naturally biotinylated proteins was used in mammalian cells ([Parrott and Barry, 2000] and [Parrott and Barry, 2001]). Small peptide tags obtained by combinatorial libraries were utilized for site-specific biotinylation of a wide variety of proteins ([Tatsumi et al., 1996], [de Boer et al., 2003], [Yang et al., 2004] and [Warren et al., 2005]). There are advantages in using smaller artificial tags. First, small tags are much less likely to affect the structure and thus the properties of fusion protein in vivo. Second, artificial tags are unlikely to be recognized and biotinylated by endogenous biotin ligases. Indeed we verified that there was no cross-reactivity between the 15 aa tag and endogenous biotin ligase (FIG. 9). When comparing the two fusion proteins (Table 2) we found that, using this small BP15, metabolic biotinylation of fusion protein in eukaryotic cell is a highly efficient process that occurs in presence of ER-retained version of BirA.

Previous studies demonstrated that co-secretion of *E. coli* biotin ligase in mammalian cells resulted in biotinylation of secretory and cell surface proteins (Parrott and Barry, 2001). The present invention expands this technology to investigate the influence of location of ligase through the production of secreted and ER-retained versions. We found that the protein product directed to the lumen of ER was more efficiently biotinylated than the protein in presence of secreted ligase. For this reason we chose to metabolically biotinylate subsequent fusion proteins in the presence of ER-retained ligase. Recently a similar approach was used to label non-viral, host-derived proteins on the surface of lentiviruses using an ER-retained bacterial biotin ligase (Nesbeth et al., 2006).

More importantly the present invention provides a method of metabolically biotinylating protein in eukaryotic cells. A recent report demonstrated biotinylation of an anti-CEA scFv fragment in an *E. coli* strain over-expressing BirA (Warren et al., 2005). The limitation of this approach is that large, complex, glycosylated proteins cannot be produced in *E. coli*, whereas in the systems of the present invention, any protein, antibody or antibody fragments can be biotinylated post-translationally.

In one embodiment, the present invention provides an efficient system to metabolically biotinylate secretory polypeptides in the presence of an endoplasmic reticulum retained biotin ligase. As demonstrated in the examples of the present application, the biotinylation efficiency is >90% for the proteins with a small 15 amino acid biotin acceptor tag at the C-terminus of the diabody.

In another embodiment, the present invention provides stable cell lines expressing exogenous biotin ligase. Super-transfection of the cell line with any other fusion protein containing a biotinylation acceptor sequence allows for metabolic biotinylation of a variety of proteins, bypassing inefficient and non-specific chemical methods. The in vivo metabolic biotinylation strategies provided herein are general approaches for the production of site-specifically biotinylated proteins for avidin/streptavidin-biotin technology.

In one aspect, the present invention provides methods of producing biotinylated polypeptides. In certain embodiments, the methods comprise expressing a heterologous target polypeptide having a biotinylation acceptor sequence in a eukaryotic cell and purifying the biotinylated polypeptide from the culture supernatant. In certain embodiments the mammalian cells used in the present invention will express an exogenous biotin ligase protein that is either co-secreted with the target polypeptide or is retained in the ER of the cell. In some embodiments, the target heterologous polypeptide comprises a eukaryotic leader sequence that directs the secretion of the polypeptide.

Any biotin protein ligase known in the art may be used for the methods of the present invention. In certain embodiments, the biotin ligase may be eukaryotic, such as a yeast, fungi, insect, mammalian, human, or mouse biotin ligase. In a second embodiment, the biotin ligase may be prokaryotic, for example from a bacteria including gram-positive or gram-negative bacteria, *E. coli*, *B. subtilis*, a *Streptomyces*, a mycobacterium, a cyanobactrium, and the like. In a specific embodiment, the biotin ligase is the BirA enzyme (GenBank accession number ABG72142) from *E. coli*, or a BirA enzyme that has been engineered to contain an ER retention signal.

In one embodiment, a heterologous biotin ligase that has been engineered to be retained in the ER is provided. In certain embodiments, the heterologous biotin ligase is engineered to contain an ER retention signal such as KDEL (SEQ ID NO:16). In other embodiments, the ER retention signal may be modified to allow for both ER retention and visualization. In one specific embodiment, the ER retention signal DYKDEL (SEQ ID NO:12) may be engineered to the C-terminus of a heterologous biotin ligase, in order to facilitate both ER retention and visualization via an anti-FLAG antibody.

In one embodiment, the method of producing a biotinylated polypeptide comprises the steps of: expressing a heterologous target polypeptide having a biotinylation acceptor sequence in a eukaryotic cell, expressing in the same eukaryotic cell a heterologous biotin protein ligase that is retained in the ER, and purifying the biotinylated target polypeptide from the culture supernatant, wherein the heterologous target polypeptide is secreted from the cell. In certain embodiments, the methods further comprise supplementing the cell culture with biotin.

Many different culture mediums used for the expression of heterologous polypeptides in eukaryotic cell lines are known in the art. The skilled artisan will know how to determine an appropriate culture medium for use in the methods provided by the present invention. Factors that may be considered in the determination of an appropriate medium include, without limitation, the cell origin to be used for expression, the heterologous polypeptide being expressed, the length of the desired culturing, the culture conditions, and the like.

In certain embodiments, the medium used in the methods of the present invention may be supplemented with biotin. In a particular embodiment, the medium may be supplemented with from about 1 µM to about 10 mM biotin. In other embodiments, the medium used in the methods of the invention may comprises from about 10 µM to about 1000 µM biotin or from about 20 µM to about 500 µM, or from about 50 µM to about 500 µM biotin, or from about 50 µM to about 200 µM biotin, or in a range similar thereof. In yet other particular embodiments, the methods of the invention comprise supplementing the culture medium with at least about 1 µM biotin, or with at least about 5, 10, 25, 50, 75, 100, 125, 150, 200, 250, 300, 400, 500, 600, 700, 800, 900, 1000 µM or more biotin.

Biotinylation acceptor sequences suitable for use in the present invention are well known in the art and include any naturally occurring sequence or polypeptide, such as the 123 amino acid biotin acceptor domain (BD 123) of *P. shermanii* or the biotin carboxyl carrier protein (BCCP) subunit of *E. coli* acetyl-CoA, or any synthetic sequence or polypeptide that serves as a substrate for a biotin ligase, for example the biotin AviTag™ (Beckett et al., 1999) or other known peptide substrate (Schatz, 1993). In certain embodiments of the invention, a biotinylation acceptor sequence may be at the N- or C-terminus of a heterologous target polypeptide of the invention. In other embodiments, the biotinylation acceptor sequence may be located at an internal site on the target polypeptide. In some embodiments, the biotinylation acceptor sequence may be attached to the target polypeptide through a protein linker moiety.

In certain embodiments of the invention a peptide linker can be of variable length, where, for example, the peptide linker may be from about 5 to about 50 amino acids long, or from about 5 to about 25 amino acids long, or from about 5 to about 15 amino acids long. In one embodiment, the link may be about 3, 4, 5, 6, 7, 8, 9, 10, 15, 20, 25, 30, 40, 50, or more amino acids long. In a particular embodiment, the linker may comprise a sequence selected from GSTS (SEQ ID NO:17), GSTSGS (SEQ ID NO:18), and GSTSHHHHHHGAAG (SEQ ID NO:23). In yet other embodiments of the invention, the peptide linker may comprise a protease recognition site or an ion binding site.

In yet other embodiments of the invention, a heterologous target protein of the invention may further comprise an effector moiety, such as a radioactive labels, fluorescent labels, or therapeutic moiety, such as a cytotoxic agent. In other embodiments, the biotinylated polypeptides of the invention may further comprise a tag, other than biotin, such as a His-tag, GST-tag, Strep-tag, Myc-tag, HA-tag, and the like, to further facilitate purification or visualization. In yet other embodiments, the heterologous target protein may further comprise a eukaryotic leader sequence to facilitate or promote secretion from the cell.

In some embodiments, wherein the target polypeptide comprises a cleavable linker, the methods may further comprise the steps of cleaving the linker peptide and purifying the cleaved heterologous protein away from the biotinylation acceptor sequence. In this fashion, certain embodiments of the invention provide a method of purifying a heterologous protein that is not biotinylated, but makes use of the extremely strong avidin/streptavidin-biotin interaction for purposes of purification. Accordingly, in one aspect of the invention, methods are provided for producing highly purified polypeptides suitable for pharmaceutical administration, such as recombinant antibodies, scFvs, diabodies, triabodies, and the like, which are not biotinylated.

In certain embodiments of the invention, the heterologous targets, both biotinylated and not biotinylated, of the invention comprise a pharmaceutically active agent. In some embodiments, the target protein is an antibody, minibody, diabody, triabody, scFv, and fragments thereof. Antibodies and constructs thereof provided by the invention may be useful for modifying the function of a target protein in vivo, or may be useful as a targeting agent for the delivery of a therapeutic moiety to a specific cell or tissue type.

Many eukaryotic cell lines suitable for use in the present invention are known in the art, including; yeast cells, such as a *Saccharomyces*, a *Schizosaccharomyces*, a *Candida*, a *Yarrowia*; mold cells, such as an *Aspergillus*, an *Ashbya*; plant cells, such as tobacco BY-2 cells, *Zinnia elegans* cells, *Arabidopsis thaliana* cells; animal cells, including insect cells, for example SF9 cells, SF21 cells, S2 cells, High Five cells; zebrafish ZF4 or AB9 cells, *Xenopus* A6 cells; mammalian cells, such as NSO, 3T3, RenCa, or EL4 murine cells, GH3, PC12, 9L, or B35 rat cells, BHK-21 or CHO hamster cells; primate cells, such as Vero monkey cells, COS-7 ape cells; and human cells, such as HeLa cells, 293-T cells, HEK-293 cells, H1299 cells, Jurkat cells, JY cells, and the like. One of skill in the art will know how to choose a suitable cell line for use in the methods of the present invention. Factors that may be considered when deciding on an appropriate cell or cell line choice include, without limitation, the size of the target polypeptide to be produced, the extent of post-translation modification desired, the pattern of post-translation modification, such as glycosylation, desired, the culture conditions to be used, the intended use of the target polypeptide, and the like.

In certain embodiments, the methods of the invention provide biotinylated proteins that are biotinylated with high specificity and high efficiency. In some embodiments, the biotinylation sequence of a target protein produced by the methods of the present invention may have a specificity of biotinylation of at least about 75%, or a specificity of biotinylation of at least about 80%, 85%, 90%, 95%, 96%, 97%, 98%, 99% or greater. In some embodiments, the biotinylation sequence of a target protein produced by the methods of the present invention may have an efficiency of biotinylation of at least about 75%, or an efficiency of biotinylation of at least about 80%, 85%, 90%, 95%, 96%, 97%, 98%, 99% or greater. In yet other embodiments, the biotinylated polypeptides of the invention may be biotinylated with both a specificity and efficiency at least about 80%, 85%, 90%, 95%, 96%, 97%, 98%, 99% or greater.

In yet other embodiments, the biotinylated target polypeptides of the invention may further contain post-translational modifications, such as glycosylation, phosphorylation, lipidation, ubiquitination, sumoylation, methylation, and the like. In certain embodiments, the target polypeptides of the invention may comprise post-translational modifications found in human cells or a pattern of post-translation modifications that resembles a human pattern. In a specific embodiment, a target polypeptide of the invention may comprise a glycosylation pattern that resembles a human glycosylation pattern.

In yet another embodiment of the invention, the cell cultures used in the methods of the invention may be grown to high densities. In a specific embodiment, the methods of the invention may comprise expression of a target polypeptide in a culture that is grown to confluence. In yet other embodiments, the expression methods of the invention may comprise maintaining high levels of expression or secretion of a target polypeptide for long periods of time. In certain embodiments, the methods comprise stable expression of a target polypeptide for at least about 2 days, in other embodiments, the expression or secretion may remain stable for at least about 3, 4, 5, 6, 7, 8, 9, 10, 11, 12, 13, 14, or more days. In some embodiments of the invention, the methods comprise periodic harvesting of the culture supernatant, followed by purification of the secreted biotinylated target polypeptides.

In a specific embodiment of the invention, a method of producing a biotinylated polypeptide is provided, the method comprising the steps of: expressing a heterologous target polypeptide having a biotinylation acceptor sequence in a eukaryotic cell, expressing in the same eukaryotic cell a heterologous biotin protein ligase that is retained in the ER, periodically harvesting and replacing the culture supernatant, and purifying the biotinylated heterologous target polypeptide from the culture supernatant, wherein, the biotinylated heterologous target polypeptide is secreted from the cell, and the heterologous target polypeptide is expressed for at least about 5 days. In certain embodiments, periodic harvesting may comprise at least every other day, or at least once a day or at least about 2, 3, 4, 5, 6, or more times a day. In other embodiments, the cell culture may be supplemented with biotin.

In another aspect of the invention, eukaryotic cells and cell lines are provided for use in the methods of the present invention. In one embodiment, a cell line is provided for the production of a secreted heterologous biotinylated polypeptide, wherein said cell line expresses a heterologous biotin ligase having an ER retention sequence, and secretes a heterologous target protein having a biotinylation acceptor sequence and a eukaryotic leader sequence for extracellular secretion. In certain embodiments, the cell lines of the invention produce target polypeptides wherein the biotinylation acceptor sequence is biotinylated with at least about 90% specificity and at least about 90% efficiency. In yet other embodiments, the cell lines of the invention provide stable expression and stable secretion at least about 2, 3, 4, 5, 6, 7, 8, 9, 10, 11, 12, 13, 14, or more days.

The present invention also provides kits to facilitate and/or standardize use of compositions provided by the present invention, as well as facilitate the methods of the present invention. Materials and reagents to carry out these various methods can be provided in kits to facilitate execution of the methods. As used herein, the term "kit" is used in reference to a combination of articles that facilitate a process, assay, analysis or manipulation.

Kits can contain chemical reagents (e.g., biotin, components of a culture media, etc.) as well as other components. In addition, kits of the present invention can also include, for example but not limited to, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, instructions to the kit user, solutions, buffers or other chemical reagents, suitable samples to be used for standardization, normalization, and/or control samples. Kits of the present invention can also be packaged for convenient storage and safe shipping, for example, in a box having a lid.

In some embodiments, the kits of the present invention may comprise a eukaryotic cell line of the invention, a system for the production of a biotinylated target polypeptide, an expression vector for a target polypeptide, reagents for further modifying or conjugating purified biotinylated proteins of the invention, and the like.

DEFINITIONS

As used herein, the term "biotinylation acceptor sequence" or "biotin acceptor tag" refers to a polypeptide or amino acid sequence which is selectively biotinylated by a biotin ligase. Biotinylation acceptor sequences may comprise synthetic polypeptides, as well as polypeptides found in nature, such as the 123 amino acid biotin acceptor domain (BD123) of *P. shermanii*, the biotin carboxyl carrier protein (BCCP) subunit of *E. coli* acetyl-CoA carboxylase, fragments thereof, or any other polypeptide that is biotinylated in nature. Alternatively, many polypeptides have been engineered as efficient substrates for biotinylation reactions performed by a host of known biotin ligase enzymes identified in all kingdoms of life (e.g., Schatz, 1993; Beckett et al., *Protein Science* (1999) 8:921-929).

As used herein, the term "specificity of biotinylation" refers to the percentage of biotinylation at a specific residue or sequence in a protein, for example at a biotinylation acceptor sequence, as compared to the total biotinylation of the protein. Thus, if 9 out of every 10 biotinylation events occur at a single location in a population of a specific protein, for example at a biotinylation acceptor sequence, the residue or sequence would be biotinylated with 90% specificity. In certain embodiments of the invention, the specificity of biotinylation for a recombinant protein may be at least about 50%. In other embodiments, the specificity of biotinylation for a recombinant protein may be at least about 60%, or at least about 70%, 75%, 80%, 85%, 90%, 95%, 96%, 97%, 98%, 99%, or higher.

As used herein, the "efficiency of biotinylation" refers to the percentage of target biotinylation acceptor sequences that have been biotinylated in a population of a specific protein. For example, if 9 out of every ten biotinylation acceptor sequences are biotinylated in a population, then the efficiency of biotinylation for the biotinylation acceptor sequence would be 90%. In certain embodiments of the invention, the efficiency of biotinylation for a recombinant protein may be at least about 50%. In other embodiments, the efficiency of biotinylation for a recombinant protein may be at least about 60%, or at least about 70%, 75%, 80%, 85%, 90%, 95%, 96%, 97%, 98%, 99%, or higher.

As used herein, the phrase "glycosylation pattern" refers to the frequency, specificity, or location of glycosylation in a polypeptide, such as an antibody or fragment thereof. As such, a human glycosylation pattern may refer to the preferential glycosylation of a polypeptide at a specific residue or the overall pattern of glycosylation throughout a polypeptide, which would be found in a human cell.

As used herein, the phrase "extended production" of a protein or polypeptide refers to the sustained expression or sustained secretion of a polypeptide from a culture of cells over a period of more than one day. In certain embodiments, the extended production of a recombinant protein may comprise expression or secretion of the polypeptide for at least about 2 days. In other embodiments, the extended production of a recombinant protein may comprise expression or secretion of the polypeptide for at least about 3, 4, 5, 6, 7, 8, 9, 10, 11, 12, 13, 14, 15, 16, 17, 18, 19, 20, 21, 25, 30, 35, 40, 50, or more days.

As used herein, a "eukaryotic leader sequence" or "leader sequence" used for extracellular excretion refers to a short amino acid sequence that directs the secretion of a polypeptide in a eukaryotic cell. Generally, proteins destined for secretion are directed into the ER by a eukaryotic leader sequence, usually comprising about 15 to about 25 amino acids in length. The mRNA encoding a polypeptide destined for secretion is translated by a ribosome which is initially free in the cytoplasm of the producing cell, but, translocates to the ER as the leader sequence emerges from the ribosome. Eukaryotic leader sequences are well known in the art. The skilled artisan will know how to choose an appropriate leader sequence for use in the present invention, dependent upon several factors including the expression conditions and origin of the cell line used for the production of the recombinant polypeptides of the invention.

As used herein, the term "periodically" refers to an event that occurs more than once, or at regular intervals. In terms of the present invention, periodic may refer to an event that occurs, for example, at least once a week, or it may refer to an event that occurs at least about 2, 3, 4, 5, 6 or more times a week. In yet other embodiments, periodically may refer to an event that occurs at least once a day, or at least about 1, 2, 3, 4, 5, 6, 7, 8, or more times a day.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing. isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, ÿ-carboxyglutamate, and O-phosphoserine. Amino acid analogs refers to compounds that have the same basic chemical structure as a naturally occurring amino acid, i.e., an ÿ carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

Accordingly, the term antibody also embraces minibodies, diabodies, triabodies and the like. Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., *J Nucl Med* 44:1962-9 (2003). In addition, these antibodies are advantageous because they can be engineered if necessary as different types of antibody fragments ranging from a small single chain Fv to an intact IgG with varying isoforms (Wu & Senter, *Nat. Biotechnol.* 23:1137-1146 (2005)). In some embodiments, the antibody fragment is part of a diabody.

Diabodies, first described by Hollinger et al., PNAS (USA) 90(14): 6444-6448 (1993), may be constructed using heavy and light chains, as well as by using individual CDR regions. Typically, diabody fragments comprise a heavy chain variable domain ($V_H$) connected to a light chain variable domain ($V_L$) by a linker which is too short to allow pairing between the two domains on the same chain. Accordingly, the $V_H$ and $V_L$ domains of one fragment are forced to pair with the complementary $V_H$ and $V_L$ domains of another fragment, thereby forming two antigen-binding sites. Triabodies can be similarly constructed with three antigen-binding sites. An Fv fragment contains a complete antigen-binding site which includes a $V_L$ domain and a $V_H$ domain held together by non-covalent interactions. Fv fragments embraced by the present invention also include constructs in which the $V_H$ and $V_L$ domains are crosslinked through glutaraldehyde, intermolecular disulfides, or other linkers. The variable domains of the heavy and light chains can be fused together to form a single chain variable fragment (scFv), which retains the original specificity of the parent immunoglobulin. Single chain Fv (scFv) dimers, first described by Gruber et al., *J. Immunol.* 152(12):5368-74 (1994), may be constructed using heavy and light chains, as well as by using individual CDR regions. Many techniques known in the art can be used to prepare the specific binding constructs of the present invention (see, U.S. Patent Application Publication No. 20070196274 and U.S. Patent Application Publication No. 20050163782, which are each herein incorporated by reference in their entireties for all purposes, particularly with respect to minibody and diabody design).

Bispecific antibodies can be generated by chemical cross-linking or by the hybrid hybridoma technology. Alternatively, bispecific antibody molecules can be produced by recombinant techniques (see: bispecific antibodies). Dimerization can be promoted by reducing the length of the linker joining the $V_H$ and the $V_L$ domain from about 15 amino acids, routinely used to produce scFv fragments, to about 5 amino acids. These linkers favor intrachain assembly of the $V_H$ and $V_L$ domains. A suitable short linker is GGGSGGGG (SEQ ID NO:19) but other linkers can be used. Thus, two fragments assemble into a dimeric molecule. Further reduction of the linker length to 0-2 amino acids can generate trimeric (triabodies) or tetrameric (tetrabodies) molecules.

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4:72 (1983); Cole et al., in *Monoclonal Antibodies and Cancer Therapy*, Alan R. Liss, Inc., pp. 77-96 (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In some embodiments, a recombinant polypeptide provided by the invention may be further conjugated to an "effector" moiety. The effector moiety can be any number of molecules, including labeling moieties such as radioactive labels or fluorescent labels, or can be a therapeutic moiety. In one aspect the antibody modulates the activity of the protein. Such effector moieties include, but are not limited to, an anti-tumor drug, a toxin, a radioactive agent, a cytokine, a second antibody or an enzyme. Further, the invention provides an embodiment wherein the antibody of the invention is linked to an enzyme that converts a prodrug into a cytotoxic agent.

Techniques for conjugating therapeutic agents to constructs according to the invention are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. These control elements may be designed to allow the clinician to turn off or on the expression of the gene by adding or controlling external factors to which the regulatory elements are responsive.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher et al., *J. Biol. Chem.* 273(52):35095-35101 (1998).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36 C is typical for low stringency amplification, although annealing temperatures may vary between about 32 C and 48 C depending on primer length. For high stringency PCR amplification, a temperature of about 62 C is typical, although high stringency annealing temperatures can range from about 50 C to about 65 C, depending on the primer length and specificity. Typical cycle conditions for both high and low stringency amplifications include a denaturation phase of 90 C-95 C for 30 sec-2 min., an annealing phase lasting 30 sec.-2 min., and an extension phase of about 72 C for 1-2 min. Protocols and guidelines for low and high stringency amplification reactions are provided, e.g., in Innis et al. (1990) *PCR Protocols, A Guide to Methods and Applications*, Academic Press, Inc. N.Y.).

A biotinylated polypeptide of the invention can have a label or detectable moiety, in addition to biotin, attached thereto. A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Overexpression" refers to RNA or protein expression in a cell or cell line, that is significantly higher that RNA or protein expression of in a control cell or cell line. The terms "overexpress," "overexpression" or "overexpressed" interchangeably refer to a gene that is transcribed or translated at a detectably greater level in a first cell or cell line, for example in a recombinant cell line of the invention, in comparison to a second cell or cell line that does not harbor an expression construct of the invention. Overexpression, therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Overexpression can also be by 50%, 60%, 70%, 80%, 90% or more (2-fold, 3-fold, 4-fold). The overexpression may be based upon visually detectable or quantifiable differences observed using immunohistochemical methods to detect an engineered protein or nucleic acid of the invention.

EXAMPLES

Example 1

The present example describes the assembly of genes encoding diabody fusion proteins (Db-BD123 and Db-BP15).

To construct Db-BD123 fusion protein (FIG. 1A), the sequence encoding the 123 amino acid biotin acceptor domain (BD123) of *P. shermanii* (SEQ ID NO:2) was amplified by PCR from pBGLuc-birA (kindly provided by Verhaegent and Christopoulos, 2002) using the BD-forward and BD-reverse primers shown in Table 1. The gel purified PCR product was inserted downstream from the anti-CEA Db (Wu et al., 1999) in the pEE12 mammalian expression vector (Lonza Biologics, Slough, UK) (Bebbington et al., 1992) using SpeI and EcoRI sites. The resulting construct Db-BD123 was also inserted into the pcDNA3.1 neo vector (Invitrogen, Carlsbad, Calif.) using XbaI and EcoRI sites.

Three additional variants of the Db-BP15 (FIG. 1A) were made using the 15 aa sequence, GLNDIFEAQKIEWHE (SEQ ID NO:1) (Biotin AviTag™), BirA substrate peptide (Beckett et al., 1999) at the C-terminus of diabody. One variant contained the anti-CEA Db directly fused to the 15 aa biotinylation tag (Db-BP15). The other two variants contained a 6xHis (SEQ ID NO:24) tag that either preceded (Db-His-BP15) or followed the 15 aa biotinylation tag (Db-BP15-His) (FIG. 1A). These tags were also inserted into pEE12 downstream of the anti-CEA Db as SpeI-EcoRI fragments. All constructs included a mammalian leader sequence at their N-terminus for extracellular secretion.

Example 2

The present example details the design of secreted and ER-retained enzyme biotin ligase (BirA).

The *E. coli* BirA gene was amplified from the pBGLuc-birA vector (Verhaegent and Christopoulos, 2002) by two separate reactions using the primers listed in Table 1. In the first reaction, primers birA10 and birA11/12 were used. The PCR product was gel purified and used as template in the subsequent amplification with birA20 and birA21/22 primers (Table 1). The final PCR products encoding secretory BirA-DYKD (SEQ ID NO: 13) and ER retained BirA-DYKDEL (SEQ ID NO:14) (FIG. 1B) were gel purified and cloned into the pEE12 vector using XbaI and EcoRI sites. The DYKD (SEQ ID NO:11) sequence is the truncated form of the FLAG epitope tag (DYKDDDDK) (SEQ ID NO:15), which allows detection of the recombinant proteins using the M2 anti-FLAG antibody (Sigma-Aldrich, St. Louis, Mo.) and KDEL (SEQ ID NO:16) provides an ER retention signal ([Munro and Pelham, 1987], [Beerli et al., 1994a] and [Beerli et al., 1994b]).

Example 3

The present example demonstrates the mammalian expression, selection, and purification of secreted and ER-retained enzyme biotin ligase (BirA) and diabody constructs.

In order to examine the biotinylation of protein secreted from cells, biotin ligase (BirA-DYKD) (SEQ ID NO:13) was co-secreted with the fusion protein of interest, anti-CEA Db-BD123. First, BirA-DYKD (SEQ ID NO:13) was transfected into NS0 cells and clones stably expressing high levels of BirA were identified by Western blot. FIG. 2A shows three representative clones (1D9, 1 G6 and 3G7) expressing BirA-DYKD (SEQ ID NO:13) as judged by molecular weight (35.5 kDa) and by anti-FLAG M2 antibody reactivity.

The apparent highest expressing clone, 1G6, was super-transfected with pcDNAneo/Db-BD123 construct. A Western blot probed with anti-Fab antibody shows a single band of 42 kDa, corresponding to combined mass of anti-CEA scFv (27 kDa) and BD123 (15.1 kDa) (FIG. 2B). Staining with SA HRP demonstrated that the Db-BD123 protein could be metabolically biotinylated by the secreted biotin protein ligase (FIG. 2C). The expression level of Db-BD123 (average of four clones) ranged from 4 to 6 μg/ml in T-flasks as determined by ELISA.

TABLE 1

PCR Primers.

| Primer | Sequence | SEQ ID NO: | Restriction Site |
|---|---|---|---|
| BD-forward | CGGA*CTAGT*ATGAAACTGAAGGTAACAGTCAACGGC | 3 | SpeI |
| BD-reverse | CCG*GAATTC*GCGGCCGCCTATCATTCGATGAGCTCGAGATCCCC | 4 | EcoRI |
| birA10 | CTATGGGTGCTGCTGCTCTGGGTTCCAGGTTCCACCCGGTATGAAGGATAACACCGTGCCAC | 5 | |
| birA11 (DYKD) (SEQ ID NO: 11) | ATCTTTGTAATCTTTTTCTGCACTACGCAGGGATATTTC | 6 | |
| birA12 (DYKDEL) (SEQ ID NO: 12) | CAGTTCATCTTTGTAATCTTTTTCTGCACTACGCAGGGATATTTC | 7 | |
| birA20 | GCG*GAATTCTCTAGA*GCCGCCACC**ATGGAGACAGACACACTCCTGCTATGGGTGCTGCTGCTCTGGG | 8 | XbaI |
| birA21 (DYKD) (SEQ ID NO: 11) | CCG*GAATTC*GCGGCCGCCTATCAATCTTTGTAATCTTTTTCTGCAC | 9 | EcoRI |
| birA22 (DYKDEL) (SEQ ID NO: 12) | CCG*GAATTC*GCGGCCGCCTATCACAGTTCATCTTTGTAATCTTTTTC | 10 | EcoRI |

Restriction sites are shown in italics, stop codons are underlined and Kozak consensus sequence is in boldface type.

Briefly, NS0 murine myeloma cells (Galfre and Milstein, 1981) were transfected and subjected to selection in glutamine deficient medium as described previously ([Yazaki et al., 2001] and [Yazaki and Wu, 2003]). Cells transfected with the pEE12/Db-BD123 construct were supplemented with biotin (Sigma-Aldrich) to a final concentration of 100 µM. For supertransfection, NS0 cells were first transfected with BirA-DYKD (SEQ ID NO:13) and selected in glutamine deficient medium. The expression of BirA-DYKD (SEQ ID NO:13) was detected by Western blot using anti-FLAG M2 peroxidase conjugated antibody (dilution 1:5000). The highest producing clone was supertransfected with the pcDNA-neo/Db-BD123 and double selected using glutamine deficient medium and 1 mg/ml of G418 (Calbiochem, San Diego, Calif.).

Clones were screened for expression of diabody by ELISA, in which the desired protein was captured by Protein L and detected by alkaline phosphatase (AP)-conjugated goat anti-mouse Fab antibody (Sigma-Aldrich) as described (Olafsen et al., 2004). Supernatants were also analyzed by Western blot using AP-conjugated goat anti-mouse Fab antibody (Sigma-Aldrich, dilution 1:5000) to detect the diabody, mouse monoclonal IgG1 Penta-His antibody (Qiagen, Valencia, Calif., dilution 1:1000) to detect the 6xHis (SEQ ID NO:24) tag, and streptavidin horseradish peroxidase conjugate (SA HRP) (GE Healthcare, Piscataway, N.J., dilution 1:2000) to detect biotin. The highest expressing clones were expanded into triple flasks (Nunclon, Rochester, N.Y.). Supernatants containing the anti-CEA Db-BD123 fusion protein were loaded onto a Protein L column (Pierce, Rockford, Ill.). Bound protein was eluted using 0-100% gradient of 0.1 M glycine (pH 2.5) in PBS (pH 7.0). Eluted fractions were collected in the presence of 1/10 volume of 2 M Tris-HCl pH 8.0. Hexahistidine (SEQ ID NO:24)-tagged Db-BP15-His fusion protein was purified by Ni-NTA chromatography (Qiagen). Bound proteins were eluted with 250 mM imidazole in presence of PBS (pH 7.0), 300 mM NaCl and 0.1% TritonX-100. Eluted fractions containing the desired protein were pooled, dialyzed against PBS and concentrated by Centriprep 30 (Millipore Corp., Bedford, Mass.). The final concentration of purified proteins was determined by $A_{280\ nm}$ using an extinction coefficient $\epsilon=1.5$. The expression level of recombinant diabody in T-flasks was determined by ELISA using anti-CEA diabody as a standard. The protein was captured by Protein L in microtiter plates and detected by AP-conjugated goat anti-mouse Fab antibody (Sigma-Aldrich).

Example 4

The present example outlines the characterization of purified biotinylated protein.

Purified proteins were analyzed by SDS-PAGE under non-reducing conditions. Samples were also subjected to gel filtration chromatography on a Superdex 75 HR 10/30 column (GE Healthcare) that was run isocratically in 50 mM $Na_3PO_4$, 0.15 mM NaCl (pH 7.0). Retention times were compared with that of the parental diabody. The Db-BD123 fusion protein was also subjected to gel filtration chromatography on a Superdex 200 HR 10/30 column (GE Healthcare) in 50 mM $Na_3PO_4$, 0.15 mM NaCl (pH 7.0). Retention time was compared with standards of anti-CEA intact chimeric T84.66 antibody, minibody and diabody as described (Kenanova et al., 2005). Proteins were detected by absorbance at 280 nm.

Example 5

The present example describes the efficient metabolic biotinylation of Db-BD123 by ER-retained biotin ligase.

Figure 3:
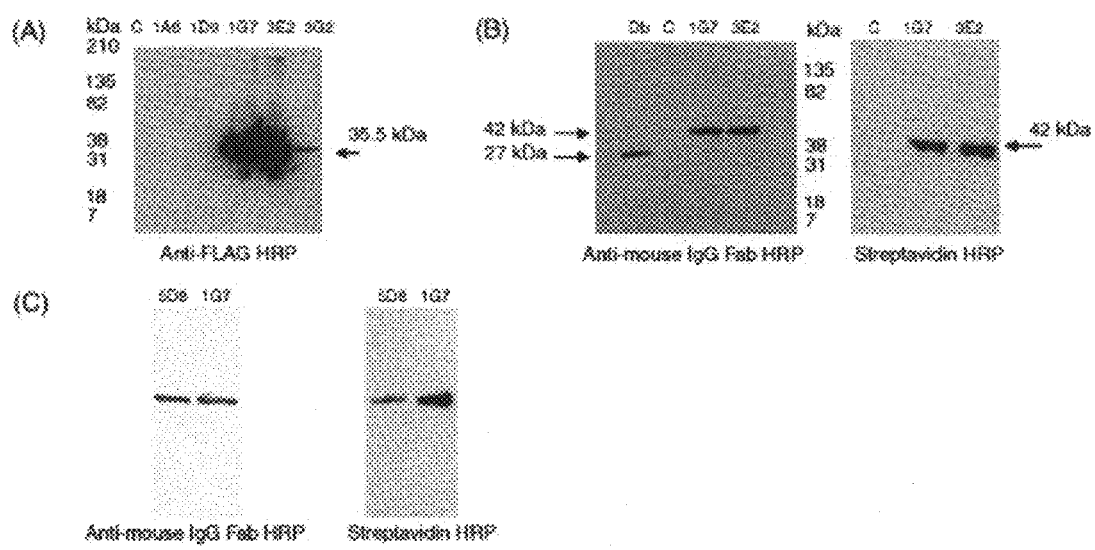
FIG. 3. In vivo biotinylation of Db-BD123 fusion protein cotransfecting with ER-retained biotin ligase (BirA-DYKDEL) (SEQ ID NO:14). (A) Western blot of BirA-DYKDEL (SEQ ID NO:14) expression in total cell lysate (5 μg per lane). Expression was detected with anti-FLAG M2 antibody. C, total cell lysate from non-transfected NS0 cells. (B) Western blots of media supernatants from NS0 cells expressing Db-BD123 using HRP-conjugated anti-mouse Fab and with SA HRP. C, the supernatant from non-transfected NS0 cells. Db, diabody (positive control). (C) Biotinylation efficiency of Db-BD123 by secretory (5D8) and ER-retained (1G7) ligase. Equal amount of proteins were loaded in each lane. Diabody was detected with anti-mouse Fab antibody and biotin was detected with SA HRP.

The ER-retained version of biotin ligase (BirA-DYKDEL) (SEQ ID NO:14) was stably cotransfected with the Db-BD123 construct into NS0 myeloma cells. Western blots with anti-FLAG antibody demonstrated stable expression of BirA in cell lysates (FIG. 3A). Furthermore Western blot analysis of supernatants showed the presence of the biotinylated Db-BD123 (FIG. 3B).

To evaluate the efficiency of biotinylation by secreted ligase versus ER-retained ligase, we compared the extent of biotinylation of two Db-BD 123 proteins produced by co-secretion with ligase (5D8) and ER-retained ligase (1G7). FIG. 3C shows that the expression of the diabody moiety is similar for both proteins; whereas the extent of biotinylation differs (the ratio of signals was 1:8 by densitometry). Analysis of additional clones expressing biotinylated Db-BD123 (3A2, 7H5 from FIGS. 2B and C) confirmed that ER-retained ligase biotinylated more efficiently than secreted ligase (data not shown).

Example 6

The present example demonstrates the biotinylation of a short biotin acceptor peptide.

Figure 4:
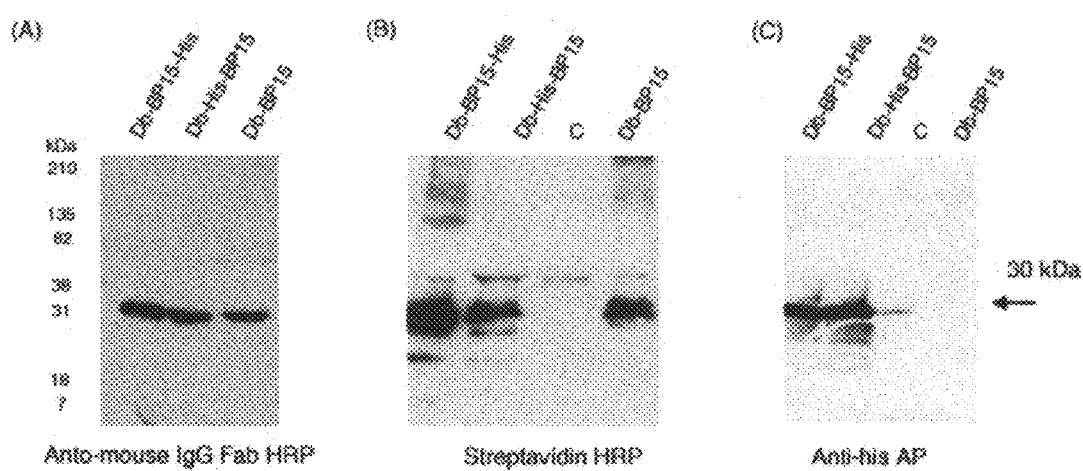
FIG. 4. Western blots of media supernatants from NS0 cells expressing Db-BP15 using HRP-conjugated anti-mouse Fab and with SA HRP. The presence of 6×His (SEQ ID NO:24) tag was detected with AP-conjugated anti-His antibody. C, the supernatant from non-transfected NS0 cells.

Three versions of diabody fused to a 15 aa biotin acceptor peptide (Db-BP15, Db-His-BP15 and Db-BP15-His) were coexpressed with BirA-DYKDEL (SEQ ID NO:14). As seen in FIG. 4, diabody fusion protein was expressed in culture supernatants (FIGS. 4A and C) and biotinylation was confirmed by probing Western blot with SA HRP (FIG. 4B). Hence, the 15 amino acid short biotin acceptor peptide is sufficient for biotinylation. Since there was no obvious difference in the expression and biotinylation of two versions of Db-BP 15 containing 6xHis tag, the cell line expressing Db-BP 15-His was selected for further study.

Example 7

The present example shows the purification and biochemical characterization of Db-BD123 and Db-BP15-His protein.

Figure 5:
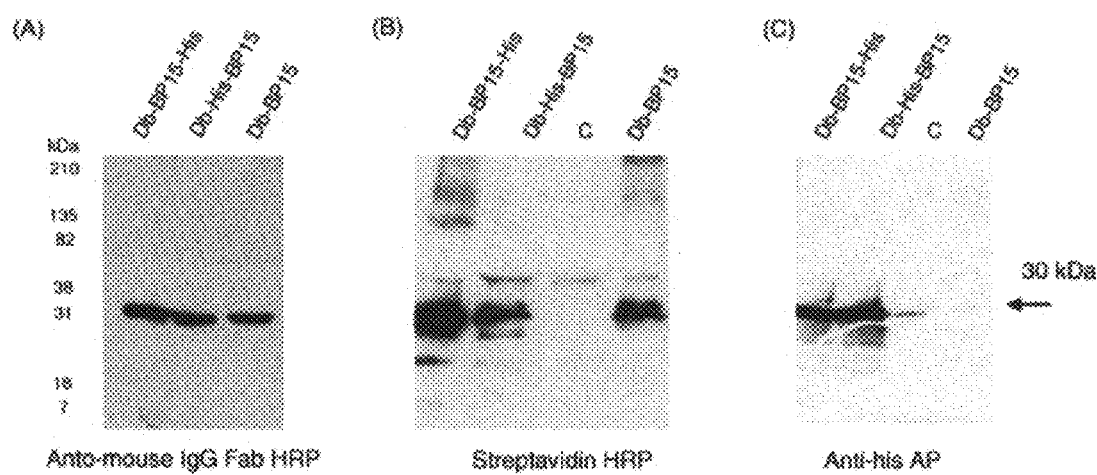
FIG. 5. Biochemical characterization of purified biotinylated anti-CEA diabody fusion proteins. (A) SDS-PAGE. Lane 1, Db-BP15-His; lane 2, Db-BD123; lane 3, molecular weight markers. (B) Size-exclusion analysis using Superdex 75 HR column. The major peaks eluted at retention times of 18.33 min for Db-BD123 and 20.70 min for Db-BP15 consistent with dimers of 84 and 60 kDa, respectively. The parental anti-CEA diabody (55 kDa; Wu et al., 1999) was used as size standard. (C) Size-exclusion analysis of purified Db-BD123 using a Superdex 200 HR column. The major peak eluted at retention time of 28.79 min. Intact chimeric T84.66 IgG (150 kDa; Neumaier et al., 1990), minibody (80 kDa; Hu et al., 1996) and diabody (55 kDa) with the corresponding retention times of 25.8, 28.5 and 38.2 min were used as size standards. Proteins were detected by absorbance at 280 nm.

The expression levels in culture supernatants were 15-20 µg/ml for Db-BD123 and 18-22 µg/ml for Db-BP15-His. A volume of 300 ml culture supernatants containing Db-BD123 and Db-BP15-His yielded 4.5 and 6.12 mg of pure protein, respectively, representing 80-90% recovery. FIG. 5A shows that the migration of the fusion proteins was consistent with the predicted molecular weight of a monomer of 30 kDa for Db-BP15-His (lane 1) and 42 kDa for Db-BD123 (lane 2).

Size exclusion chromatography was performed to evaluate the native state of biotinylated fusion proteins. The chromatogram from Superdex 75 HR column (FIG. 5B) shows that the Db-BP15-His elutes at approximately the same time as that of diabody (at 20.70 min) demonstrating that the Stokes' radius of this fusion protein is not significantly changed by the addition of the short 15 aa biotin acceptor peptide and the 6xHis (SEQ ID NO:24) tag. On the other hand, Db-BD123 elutes as a single peak at 18.33 min and earlier than that of the diabody alone (20.69 min) as expected. When Db-BD123 protein was further analyzed on a calibrated Superdex 200 HR 10/30 column (FIG. 5C), main peak eluted at 28.79 min corresponding to an approximate molecular weight of 80-85 kDa.

Example 8

The present example describes the functional characterization of biotinylated anti-CEA diabody fusion proteins.

Figure 6:
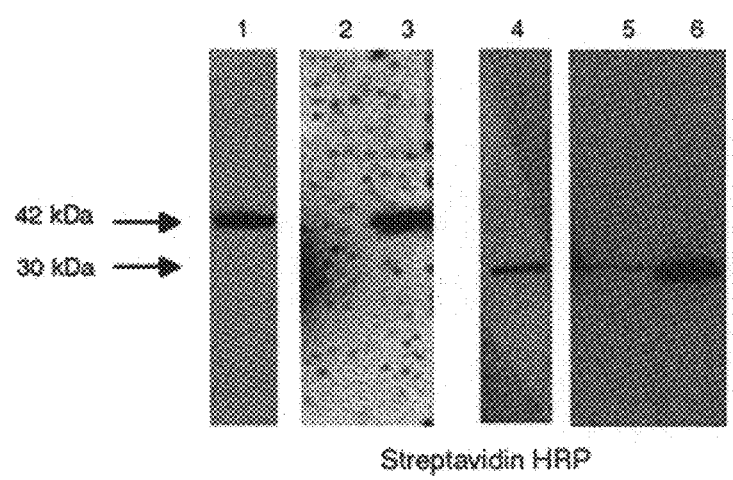
FIG. 6. Efficiency of biotinylation. Western blot using SA HRP to detect binding of biotinylated fusion proteins to streptavidin agarose. Lanes 1 and 4, starting material; lanes 2 and 5, unbound material; lanes 3 and 6, streptavidin bound material.

A critical issue is the efficiency of biotinylation of the target protein by the coexpressed ER-retained ligase. Fusion proteins were immunoprecipitated by streptavidin agarose beads and analyzed by Western blot. Most of the Db-BD 123 protein bound to the beads (FIG. 6, lanes 2 and 3) and only about 10% of Db-BP15-His protein remained unbound (lanes 5 and 6). This demonstrates that the fusions proteins are efficiently biotinylated (>90%) and can be captured by streptavidin agarose beads.

Briefly, fifty microliters of ImmunoPure streptavidin coated beads (Pierce) were used for 3.5 µg of purified protein. Binding was done in PBS at room temperature for 1 h on a rocking platform, followed by three washes in PBS. Bound material was eluted by boiling for 5 min in protein sample loading buffer and analyzed by Western blot using SA HRP antibody for detection.

Figure 7:
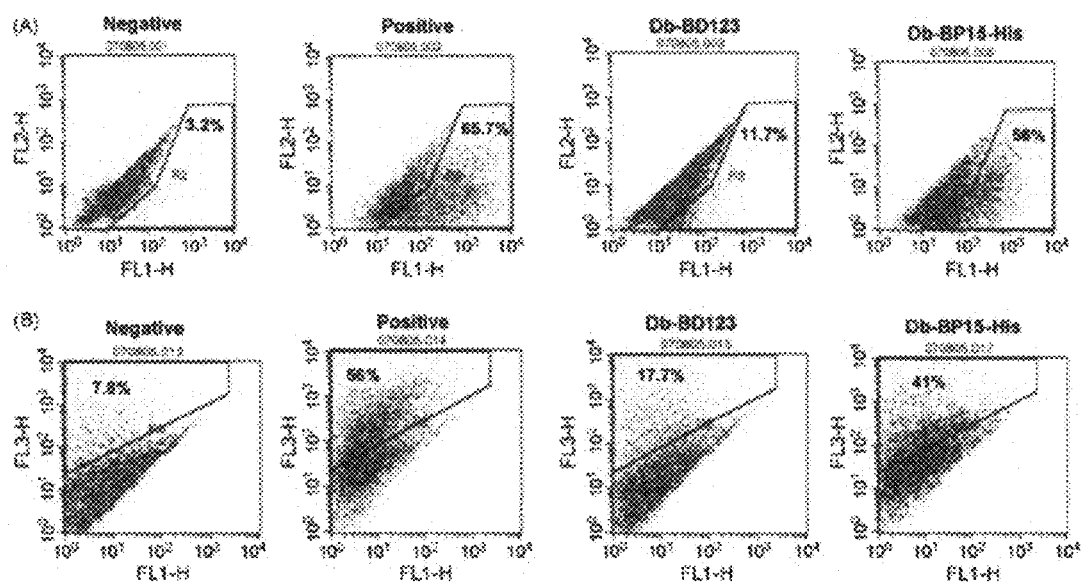
FIG. 7. Flow cytometry of purified fusion proteins binding to live LS174T-CEA⁺ cells. Cells were incubated with no protein (negative control), in vitro biotinylated chimeric T84.66 antibody (positive control) and purified biotinylated fusion proteins (Db-BD123 and Db-BP15-His). The cells were stained with (A) Alexa Fluor 488 conjugated streptavidin (FL1, horizontal shift) and (B) Qdot655SA (FL3, vertical shift).

To ensure that the addition of the biotin acceptor peptide and/or biotinylation did not affect the properties of the tagged proteins, binding of biotinylated diabodies was assessed on live LS174T colon carcinoma cells using Alexa Fluor 488 conjugated streptavidin. Flow cytometric analysis showed that in vivo biotinylated Db-BP15-His stained better (56%) than the full length Db-BD123 fusion protein (11.7%) (FIG. 7A). In comparison, biotinylated intact anti-CEA chimeric T84.66 antibody showed 65.7% positive staining. Binding of biotinylated anti-CEA diabodies to LS174T cells was also detected using Qdot655SA. Again Db-BP15-His stained better than Db-BD123 (41% versus 17.7%), and was comparable to parental chimeric T84.66 (56%).

Briefly, LS174T-CEA$^+$ human colon carcinoma cells (ATCC, Manassas, Va.; #CCL-188), were incubated with purified Db-BD123 or Db-BP15-His fusion protein for 1 h at 4° C. in PBS containing 1% BSA. The presence of biotin in the fusion protein was detected by incubation with Alexa Fluor 488 conjugated streptavidin (Molecular Probes Inc., Eugene, Oreg.) (dilution 1:5000 in PBS Tween 20) or Quantum dot 655 streptavidin conjugate (Qdot655SA) (Quantum Dot Corp., Hayward, Calif.). Antibody binding to CEA was quantified by FACS Calibur flow cytometer (Beckton Dickinson, UK) and data were analyzed by Cell Quest software. FL1 ($\lambda_{em}$: 530/30 nm) and FL3 ($\lambda_{em}$: 670 nm long pass) were the filters used for Alexa Fluor 488 and Qdot 655, respectively. Biotinylated chimeric T84.66 antibody prepared using an EZ-Link Sulfo-NHS-LC-Biotinylation kit (Pierce) was used as a positive control.

Figure 8:
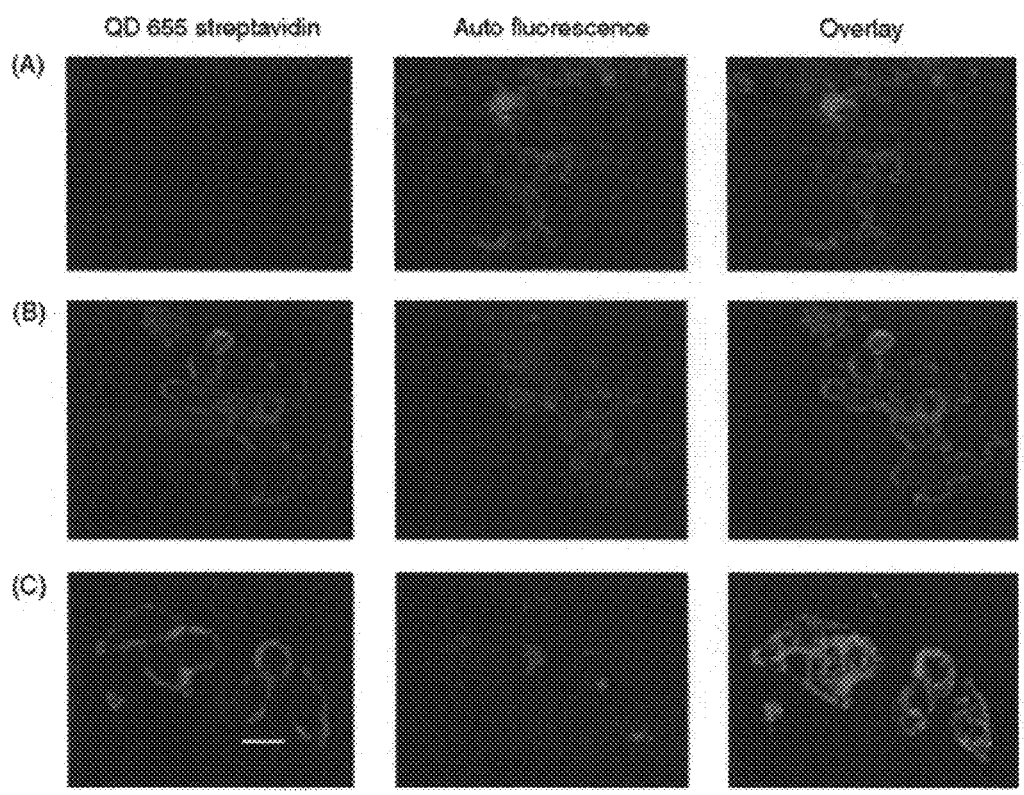
FIG. 8. Fluorescence micrographs of LS174T-CEA⁺ cells following incubation with purified fusion protein (Db-BD123 or Db-BP15-His) and Qdot655SA. Cells were imaged in a confocal microscope. LS174T-CEA⁺ cells treated with (A) no protein (negative control), (B) Db-BD123 and (C) Db-BP15-His. The scale bar corresponds to 20 μm.

The binding of biotinylated fusion proteins was also demonstrated by confocal microscopy using Qdot655SA. The immunofluorescence result showed bright surface staining of LS174T cells when the cells were incubated with Db-BD123 (FIG. 8B) and Db-BP15-His (FIG. 8C) followed by Qdot655SA compared to Qdot655SA alone (FIG. 8A).

Briefly, LS174T-CEA$^+$ cells were plated on poly-1-lysine coated glass coverslips (BD Biosciences, San Jose, Calif.) in 12 well-plates in DMEM medium containing 5% fetal bovine serum (FBS) for 24 h. The next day, cells were incubated with 2 µg/ml of Db-BD123 or Db-BP15-His fusion protein in PBS/1% FBS on ice for 1 h. Cells were then fixed with 3.7% paraformaldehyde at 4° C. for 30 min. After primary antibody treatment and fixation, cells were incubated in 10 nM Qdot655SA in PBS/1% FBS at room temperature for 1 h. Coverslips were mounted on glass slides and observed using a Leica TCS-SP inverted confocal microscope equipped with a 100× oil immersion objective lens.

It was observed that low signal was generated by Db-BD123 in flow cytometry assays using LS174T-CEA$^+$ cells (11.7% with Alexa 488 streptavidin as secondary and 17.7% with Qdot655SA as secondary). It may be possible that Db-BD123 binding to CEA sterically blocks the introduced biotin from interacting with streptavidin as replacement of BD123 with BP15 in the Db-BP15-His fusion protein improved the binding activity (Table 2).

TABLE 2

Comparison between two versions of biotinylated anti-CEA diabody.

|  | Db-BD123 | Db-BP15-His |
|---|---|---|
| Molecular weight (kDa) | 84 | 60 |
| Concentration in T flask (µg/ml) | 15-20 | 18-22 |
| Yield (%) | 80-90 | 80-90 |
| Binding with streptavidin agarose (%) | 95 | 90 |
| LS174T binding (%) | | |
| Streptavidin Alexa | 11.7 | 56 |
| Qdot streptavidin | 17.7 | 41 |

Example 9

The present example demonstrates that the biotin acceptor protein is not biotinylated in absence of exogenous biotin ligase In order to investigate whether proteins containing biotin acceptor sequences could be biotinylated by endogenous mammalian biotin ligases, NS0 cells were transfected solely with the Db-BP15-His construct. Western blots of supernatants probed with anti-mouse Fab (FIG. 9A) and anti-His (FIG. 9B) antibodies demonstrated secretion of the Db-BP15-His fusion protein. Fusion protein was not detected using SA HRP (FIG. 9C) indicating that the protein was not metabolically biotinylated by mammalian cells. This confirms that anti-CEA diabody fusion proteins are biotinylated from the introduced BirA (secreted or ER-retained form) and not by endogenous enzymes already present in the mammalian cells.

REFERENCES

Altman et al., 1996 J. D. Altman, P. A. Moss, P. J. Goulder, D. H. Barouch, M. G. McHeyzer-Williams, J. I. Bell, A. J. McMichael and M. M. Davis, Phenotypic analysis of antigen-specific T lymphocytes, Science 274 (1996), pp. 94-96.

Arnold et al., 2006 G. S. Arnold, A. K. Sasser, M. D. Stachler and J. S. Bartlett, Metabolic biotinylation provides a unique platform for the purification and targeting of multiple AAV vector serotypes, Mol. Ther. 14 (2006), pp. 97-106.

Asai et al., 2005 T. Asai, R. Trinh, P. P. Ng, M. L. Penichet, L. A. Wims and S. L. Morrison, A human biotin acceptor domain allows site-specific conjugation of an enzyme to an antibody-avidin fusion protein for targeted drug delivery, Biomol. Eng. 21 (2005), pp. 145-155.

Bayer and Wilchek, 1990 E. A. Bayer and M. Wilchek, Protein biotinylation, Methods Enzymol. 184 (1990), pp. 138-160.

Bebbington et al., 1992 C. R. Bebbington, G. Renner, S. Thomson, D. King, D. Abrams and G. T. Yarranton, High-level expression of a recombinant antibody from myeloma cells using a glutamine synthetase gene as an amplifiable selectable marker, Biotechnology (NY) 10 (1992), pp. 169-175.

Beckett et al., 1999 D. Beckett, E. Kovaleva and P. J. Schatz, A minimal peptide substrate in biotin holoenzyme synthetase-catalyzed biotinylation, Protein Sci. 8 (1999), pp. 921-929.

Beerli et al., 1994a R. R. Beerli, W. Wels and N. E. Hynes, Autocrine inhibition of the epidermal growth factor receptor by intracellular expression of a single-chain antibody, Biochem. Biophys. Res. Commun. 204 (1994), pp. 666-672.

Beerli et al., 1994b R. R. Beerli, W. Wels and N. E. Hynes, Intracellular expression of single chain antibodies reverts ErbB-2 transformation, J. Biol. Chem. 269 (1994), pp. 23931-23936.

Campos and Barry, 2004 S. K. Campos and M. A. Barry, Rapid construction of capsid-modified adenoviral vectors through bacteriophage lambda Red recombination, Hum. Gene Ther. 15 (2004), pp. 1125-1130.

Carmichael et al., 2003 J. A. Carmichael, B. E. Power, T. P. Garrett, P. J. Yazaki, J. E. Shively, A. A. Raubischek, A. M. Wu and P. J. Hudson, The crystal structure of an anti-CEA scFv diabody assembled from T84.66 scFvs in V(L)-to-V(H) orientation: implications for diabody flexibility, J. Mol. Biol. 326 (2003), pp. 341-351.

Chapman-Smith and Cronan, 1999 A. Chapman-Smith and J. E. Cronan Jr., In vivo enzymatic protein biotinylation, Biomol. Eng. 16 (1999), pp. 119-125.

Cronan, 1990 J. E. Cronan Jr., Biotination of proteins in vivo. A post-translational modification to label, purify, and study proteins, J. Biol. Chem. 265 (1990), pp. 10327-10333.

Cull and Schatz, 2000 M. G. Cull and P. J. Schatz, Biotinylation of proteins in vivo and in vitro using small peptide tags, Methods Enzymol. 326 (2000), pp. 430-440.

de Boer et al., 2003 E. de Boer, P. Rodriguez, E. Bonte, J. Krijgsveld, E. Katsantoni, A. Heck, F. Grosveld and J. Strouboulis, Efficient biotinylation and single-step purification of tagged transcription factors in mammalian cells and transgenic mice, Proc. Natl. Acad. Sci. U.S.A. 100 (2003), pp. 7480-7485.

Diamandis and Christopoulos, 1991 E. P. Diamandis and T. K. Christopoulos, The biotin-(strept)avidin system: principles and applications in biotechnology, Clin. Chem. 37 (1991), pp. 625-636.

Galfre and Milstein, 1981 G. Galfre and C. Milstein, Preparation of monoclonal antibodies: strategies and procedures, Methods Enzymol. 73 (1981), pp. 3-46.

Holliger et al., 1993 P. Holliger, T. Prospero and G. Winter, "Diabodies": small bivalent and bispecific antibody fragments, Proc. Natl. Acad. Sci. U.S.A. 90 (1993), pp. 6444-6448.

Hu et al., 1996 S. Hu, L. Shively, A. Raubitschek, M. Sherman, L. E. Williams, J. Y. Wong, J. E. Shively and A. M. Wu, Minibody: a novel engineered anti-carcinoembryonic antigen antibody fragment (single-chain Fv-CH3) which exhibits rapid, high-level targeting of xenografts, Cancer Res. 56 (1996), pp. 3055-3061.

Kenanova et al., 2005 V. Kenanova, T. Olafsen, D. M. Crow, G. Sundaresan, M. Subbarayan, N. H. Carter, D. N. Ikle, P. J. Yazaki, A. F. Chatziioannou and S. S. Gambhir et al., Tailoring the pharmacokinetics and positron emission tomography imaging properties of anti-carcinoembryonic antigen single-chain Fv-Fc antibody fragments, Cancer Res. 65 (2005), pp. 622-631.

Kojima et al., 2006 N. Kojima, T. Matsuo and Y. Sakai, Rapid hepatic cell attachment onto biodegradable polymer surfaces without toxicity using an avidin-biotin binding system, Biomaterials 27 (2006), pp. 4904-4910.

Krepkiy et al., 2006 D. Krepkiy, K. Wong, K. Gawrisch and A. Yeliseev, Bacterial expression of functional, biotinylated peripheral cannabinoid receptor CB2, Protein Expres. Purif. 49 (2006), pp. 60-70.

Kumar and Snyder, 2002 A. Kumar and M. Snyder, Protein complexes take the bait, Nature 415 (2002), pp. 123-124.

Munro and Pelham, 1987 S. Munro and H. R. Pelham, A C-terminal signal prevents secretion of luminal ER proteins, Cell 48 (1987), pp. 899-907.

Nesbeth et al., 2006 D. Nesbeth, S. L. Williams, L. Chan, T. Brain, N. K. Slater, F. Farzaneh and D. Darling, Metabolic biotinylation of lentiviral pseudotypes for scalable paramagnetic microparticle-dependent manipulation, Mol. Ther. 13 (2006), pp. 814-822.

Neumaier et al., 1990 M. Neumaier, L. Shively, F. S. Chen, F. J. Gaida, C. Ilgen, R. J. Paxton, J. E. Shively and A. D. Riggs, Cloning of the genes for T84.66, an antibody that has a high specificity and affinity for carcinoembryonic antigen, and expression of chimeric human/mouse T84.66 genes in myeloma and Chinese hamster ovary cells, Cancer Res. 50 (1990), pp. 2128-2134.

Ohno et al., 1996 K. Ohno, B. Levin and D. Meruelo, Cell-specific, multidrug delivery system using streptavidin-protein. A fusion protein, Biochem. Mol. Med. 58 (1996), pp. 227-233.

Olafsen et al., 2004 T. Olafsen, C. W. Cheung, P. J. Yazaki, L. Li, G. Sundaresan, S. S. Gambhir, M. A. Sherman, L. E. Williams, J. E. Shively and A. A. Raubitschek et al., Covalent disulfide-linked anti-CEA diabody allows site-specific conjugation and radiolabeling for tumor targeting applications, Protein Eng. Des. Sel. 17 (2004), pp. 21-27.

Parrott and Barry, 2000 M. B. Parrott and M. A. Barry, Metabolic biotinylation of recombinant proteins in mammalian cells and in mice, Mol. Ther. 1 (2000), pp. 96-104.

Parrott and Barry, 2001 M. B. Parrott and M. A. Barry, Metabolic biotinylation of secreted and cell surface proteins from mammalian cells, Biochem. Biophys. Res. Commun. 281 (2001), pp. 993-1000.

Parrott et al., 2003 M. B. Parrott, K. E. Adams, G. T. Mercier, H. Mok, S. K. Campos and M. A. Barry, Metabolically biotinylated adenovirus for cell targeting, ligand screening, and vector purification, Mol. Ther. 8 (2003), pp. 688-700.

Parthasarathy et al., 2005 R. Parthasarathy, J. Bajaj and E. T. Boder, An immobilized biotin ligase: surface display of Escherichia coli BirA on Saccharomyces cerevisiae, Biotechnol. Prog. 21 (2005), pp. 1627-1631.

Reddy et al., 1998 D. V. Reddy, S. Rothemund, B. C. Shenoy, P. R. Carey and F. D. Sonnichsen, Structural characterization of the entire 1.3S subunit of transcarboxylase from Propionibacterium shermanii, Protein Sci. 7 (1998), pp. 2156-2163.

Saviranta et al., 1998 P. Saviranta, T. Haavisto, P. Rappu, M. Karp and T. Lovgren, In vitro enzymatic biotinylation of recombinant fab fragments through a peptide acceptor tail, Bioconjug. Chem. 9 (1998), pp. 725-735.

Schatz, 1993 P. J. Schatz, Use of peptide libraries to map the substrate specificity of a peptide-modifying enzyme: a 13 residue consensus peptide specifies biotinylation in Escherichia coli, Biotechnology (NY) 11 (1993), pp. 1138-1143.

Smith et al., 1998 P. A. Smith, B. C. Tripp, E. A. DiBlasio-Smith, Z. Lu, E. R. LaVallie and J. M. McCoy, A plasmid expression system for quantitative in vivo biotinylation of thioredoxin fusion proteins in *Escherichia coli*, Nucleic Acids Res. 26 (1998), pp. 1414-1420.

Smith et al., 1999 J. S. Smith, J. R. Keller, N. C. Lohrey, C. S. McCauslin, M. Ortiz, K. Cowan and S. E. Spence, Redirected infection of directly biotinylated recombinant adenovirus vectors through cell surface receptors and antigens, Proc. Natl. Acad. Sci. U.S.A. 96 (1999), pp. 8855-8860.

Tannous et al., 2006 B. A. Tannous, J. Grimm, K. F. Perry, J. W. Chen, R. Weissleder and X. O. Breakefield, Metabolic biotinylation of cell surface receptors for in vivo imaging, Nat. Methods 3 (2006), pp. 391-396.

Tatsumi et al., 1996 H. Tatsumi, S. Fukuda, M. Kikuchi and Y. Koyama, Construction of biotinylated firefly luciferases using biotin acceptor peptides, Anal. Biochem. 243 (1996), pp. 176-180.

Tirat et al., 2006 A. Tirat, F. Freuler, T. Stettler, L. M. Mayr and L. Leder, Evaluation of two novel tag-based labelling technologies for site-specific modification of proteins, Int. J. Biol. Macromol. 39 (2006), pp. 66-76.

Tsao et al., 1996 K. L. Tsao, B. DeBarbieri, H. Michel and D. S. Waugh, A versatile plasmid expression vector for the production of biotinylated proteins by site-specific, enzymatic modification in *Escherichia coli*, Gene 169 (1996), pp. 59-64.

Verhaegen and Christopoulos, 2002 M. Verhaegen and T. K. Christopoulos, Bacterial expression of in vivo-biotinylated aequorin for direct application to bioluminometric hybridization assays, Anal. Biochem. 306 (2002), pp. 314-322.

Verhaegent and Christopoulos, 2002 M. Verhaegent and T. K. Christopoulos, Recombinant Gaussia luciferase. Overexpression, purification, and analytical application of a bioluminescent reporter for DNA hybridisation, Anal. Chem. 74 (2002), pp. 4378-4385.

Viens et al., 2004 A. Viens, U. Mechold, H. Lehrmann, A. Harel-Bellan and V. Ogryzko, Use of protein biotinylation in vivo for chromatin immunoprecipitation, Anal. Biochem. 325 (2004), pp. 68-76.

Warren et al., 2005 D. J. Warren, J. Bjemer, E. Paus, O. P. Bormer and K. Nustad, Use of an in vivo biotinylated single-chain antibody as capture reagent in an immunometric assay to decrease the incidence of interference from heterophilic antibodies, Clin. Chem. 51 (2005), pp. 830-838.

Wood and Barden, 1997 H. G. Wood and R. E. Barden, Biotin enzymes, Annu. Rev. Biochem. Allied Res. India 46 (1997), pp. 385-413.

Wu et al., 1999 A. M. Wu, L. E. Williams, L. Zieran, A. Padma, M. Sherman, G. G. Bebb, T. Odom-Maryon, J. Y. C. Wang, J. E. Shively and A. A. Raubitschek, Anti-carcinoembryonic antigen (CEA) diabody for rapid tumor targeting and imaging, Tumor Target. 4 (1999), pp. 47-58.

Wu et al., 2002 S. C. Wu, J. C. Yeung, P. M. Hwang and S. L. Wong, Design, production, and characterization of an engineered biotin ligase (BirA) and its application for affinity purification of staphylokinase produced from *Bacillus subtilis* via secretion, Protein Expres. Purif. 24 (2002), pp. 357-365.

Yang et al., 2004 J. Yang, A. Jaramillo, R. Shi, W. W. Kwok and T. Mohanakumar, In vivo biotinylation of the major histocompatibility complex (MHC) class II/peptide complex by coexpression of BirA enzyme for the generation of MHC class II/tetramers, Hum. Immunol. 65 (2004), pp. 692-699.

Yazaki and Wu, 2003 P. J. Yazaki and A. M. Wu, Construction and characterization of minibodies for imaging and therapy of colorectal carcinomas, Methods Mol. Biol. 207 (2003), pp. 351-364.

Yazaki et al., 2001 P. J. Yazaki, L. Shively, C. Clark, C. W. Cheung, W. Le, B. Szpikowska, J. E. Shively, A. A. Raubitschek and A. M. Wu, Mammalian expression and hollow fiber bioreactor production of recombinant anti-CEA diabody and minibody for clinical applications, J. Immunol. Methods 253 (2001), pp. 195-208.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of producing a biotinylated antibody, the method comprising the steps of:
   (a) expressing an antibody having a biotinylation acceptor in a eukaryotic cell, wherein the biotinylated acceptor sequence is at the N- or C-terminus of the antibody and is attached to the antibody by a linker sequence wherein the linker sequence is SEQ ID NO:17 or SEQ ID NO:18, and wherein the antibody further comprises a eukaryotic leader sequence for extracellular secretion;
   (b) expressing in the eukaryotic cell a heterologous biotin protein ligase that is retained in the eukaryotic cell endoplasmic reticulum (ER), wherein the heterologous biotin protein ligase biotinylates the antibody forming a biotinylated antibody; and wherein, the biotinylated antibody is secreted from the eukaryotic cell into a culture medium and the biotinylated antibody retains its capacity to bind antigen, and (c) purifying the biotinylated antibody from the culture medium.

2. The method of claim 1, wherein the antibody further comprises a tag to facilitate detection or purification.

3. The method of claim 1, wherein the antibody is a single chain variable fragment (scFv), a diabody, or a triabody.

4. The method of claim 1, wherein the eukaryotic cell is an insect cell, a yeast cell, or a mammalian cell.

5. The method of claim 4, wherein the insect cell is selected from the group consisting of a S2 cell, a SFM cell, a SF9 cell, a SF21 cell, or a High-Five cell.

6. The method of claim 1, wherein the mammalian cell is a human cell, a murine cell, or a hamster cell.

7. The method of claim 6, wherein the murine cell is a NS0 cell.

8. The method of claim 1, wherein the heterologous biotin protein ligase is an *E. coli* BirA ligase.

9. The method of claim 1, wherein the biotinylated antibody is glycosylated.

10. The method of claim 9, wherein the glycosylation pattern resembles a human glycosylation pattern.

11. The method of claim 1, wherein the cells are grown to confluence.

12. The method of claim 1, wherein the antibody expression is stable for at least about a week.

13. The method of claim 1, wherein the antibody is an anti-carcinoembryonic antigen (CEA) antibody.

14. The method of claim 1, wherein the culture medium is supplemented with biotin.

15. The method of claim 1, wherein the culture medium is supplemented with about 50 µM to about 500 µM biotin.

* * * * *

SEQUENCE LISTING

```
<160> NUMBER OF SEQ ID NOS: 24

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence:synthetic
      biotin acceptor sequence peptide tag, BirA
      substrate peptide biotinylation tag, BP15, Biotin
      AviTag

<400> SEQUENCE: 1

Gly Leu Asn Asp Ile Phe Glu Ala Gln Lys Ile Glu Trp His Glu
1               5                   10                  15

<210> SEQ ID NO 2
<211> LENGTH: 122
<212> TYPE: PRT
<213> ORGANISM: Artificial Sequence
<220> FEATURE:
<223> OTHER INFORMATION: Description of Artificial Sequence:synthetic
      biotin acceptor domain (BD123) of 1.3S subunit of
```

```
                          transcarboxylase domain of Propionibacterium
                          shermanii (PSTCD)

<400> SEQUENCE: 2

Met Lys Leu Lys Val Thr Val Asn Gly Thr Ala Tyr Asp Val Asp Val
  1               5                  10                  15

Asp Val Asp Lys Ser His Glu Asn Pro Met Gly Thr Ile Leu Phe Gly
                 20                  25                  30

Gly Gly Thr Gly Gly Ala Pro Ala Pro Ala Ala Gly Ala Gly Ala
             35                  40                  45

Gly Lys Ala Gly Glu Gly Glu Ile Pro Ala Pro Leu Ala Gly Thr Val
         50                  55                  60

Ser Lys Ile Leu Val Lys Glu Gly Asp Thr Val Lys Ala Gly Gln Thr
 65                  70                  75                  80

Val Leu Val Leu Glu Ala Met Lys Met Glu Thr Glu Ile Asn Ala Pro
                 85                  90                  95

Thr Asp Gly Lys Val Glu Lys Val Leu Val Lys Glu Arg Asp Ala Val
                100                 105                 110

Gln Gly Gly Gln Gly Leu Ile Lys Ile Gly
            115                 120

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence:synthetic
      PCR amplification primer BD-forward

<400> SEQUENCE: 3
cggactagta tgaaactgaa ggtaacagtc aacggc                              36

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence:synthetic
      PCR amplification primer BD-reverse

<400> SEQUENCE: 4
ccggaattcg cggccgccta tcattcgatg agctcgagat cccc                     44

<210> SEQ ID NO 5
<211> LENGTH: 61
<212> TYPE: DNA
<213> ORGANISM: Artificial Sequence
<220> FEATURE:
<223> OTHER INFORMATION: Description of Artificial Sequence:synthetic
      PCR amplification primer birA10

<400> SEQUENCE: 5
ctatgggtgc tgctgctctg ggttccaggt tccaccggta tgaaggataa caccgtgcca    60
c                                                                    61

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence:synthetic
      PCR amplification primer birA11(DYKD)

<400> SEQUENCE: 6
```

```
atctttgtaa tcttttctg cactacgcag ggatatttc                    39
```

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence:synthetic
      PCR amplification primer birA12(DYKDEL)

<400> SEQUENCE: 7

```
cagttcatct ttgtaatctt tttctgcact acgcagggat atttc            45
```

<210> SEQ ID NO 8
<211> LENGTH: 67
<212> TYPE: DNA
<213> ORGANISM: Artificial Sequence
<220> FEATURE:
<223> OTHER INFORMATION: Description of Artificial Sequence:synthetic
      PCR amplification primer birA20

<400> SEQUENCE: 8

```
gcggaattct ctagagccgc caccatggag acagacacac tcctgctatg ggtgctgctg    60
ctctggg                                                              67
```

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence:synthetic
      PCR amplification primer birA21(DYKD)

<400> SEQUENCE: 9

```
ccggaattcg cggccgccta tcaatctttg taatcttttt ctgcac           46
```

<210> SEQ ID NO 10
<211> LENGTH: 47
<212> TYPE: DNA
<213> ORGANISM: Artificial Sequence
<220> FEATURE:
<223> OTHER INFORMATION: Description of Artificial Sequence:synthetic
      PCR amplification primer birA22(DYKDEL)

<400> SEQUENCE: 10

```
ccggaattcg cggccgccta tcacagttca tctttgtaat cttttttc         47
```

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:synthetic
      C-terminus truncated form of FLAG epitope tag

<400> SEQUENCE: 11

Asp Tyr Lys Asp
1

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:synthetic
      C-terminal truncated form of FLAG epitope tag
      (DYKD) and endoplasmic reticulum (ER) retention signal (KDEL)

<400> SEQUENCE: 12

Asp Tyr Lys Asp Glu Leu
1               5

<210> SEQ ID NO 13
<211> LENGTH: 325
<212> TYPE: PRT
<213> ORGANISM: Artificial Sequence
<220> FEATURE:
<223> OTHER INFORMATION: Description of Artificial Sequence:synthetic
      secretory form of biotin ligase (BirA-DYKD), biotin protein
      ligase (BPL, BirA), holocarboxylase sythetase with C-terminal
      truncated form of FLAG epitope tag

<400> SEQUENCE: 13

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Glu Lys Ile Leu Ser Gln Leu Asp Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Val Ala Glu Tyr Gln
            100                 105                 110

His Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys Asp Tyr Lys Asp
            325

<210> SEQ ID NO 14
<211> LENGTH: 327
<212> TYPE: PRT
<213> ORGANISM: Artificial Sequence
<220> FEATURE:
<223> OTHER INFORMATION: Description of Artificial Sequence:synthetic
      endoplasmic reticulum (ER) retained form of biotin ligase
      (BirA-DYKDEL), biotin protein ligase (BPL, BirA), holocarboxylase
      sythetase with C-terminal ER retention signal and FLAG epitope tag

<400> SEQUENCE: 14

Met Lys Asp Asn Thr Val Pro Leu Lys Leu Ile Ala Leu Leu Ala Asn
 1               5                  10                  15

Gly Glu Phe His Ser Gly Glu Gln Leu Gly Glu Thr Leu Gly Met Ser
             20                  25                  30

Arg Ala Ala Ile Asn Lys His Ile Gln Thr Leu Arg Asp Trp Gly Val
         35                  40                  45

Asp Val Phe Thr Val Pro Gly Lys Gly Tyr Ser Leu Pro Glu Pro Ile
     50                  55                  60

Gln Leu Leu Asn Ala Glu Lys Ile Leu Ser Gln Leu Asp Asp Gly Ser
 65                  70                  75                  80

Val Ala Val Leu Pro Val Ile Asp Ser Thr Asn Gln Tyr Leu Leu Asp
                 85                  90                  95

Arg Ile Gly Glu Leu Lys Ser Gly Asp Ala Cys Val Ala Glu Tyr Gln
            100                 105                 110

His Ala Gly Arg Gly Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys Asp Tyr Lys Asp Glu Leu
            325

```
<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:synthetic
      FLAG epitope tag

<400> SEQUENCE: 15

Asp Tyr Lys Asp Asp Asp Asp Lys
  1               5

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence:synthetic
      endoplasmic reticulum (ER) retention signal

<400> SEQUENCE: 16

Lys Asp Glu Leu
  1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:synthetic
      peptide linker between diabody (Db) and biotin
      acceptor substrate

<400> SEQUENCE: 17

Gly Ser Thr Ser
  1

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:synthetic
      peptide linker between diabody (Db) and biotin
      acceptor substrate

<400> SEQUENCE: 18

Gly Ser Thr Ser Gly Ser
  1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:synthetic
      peptide linker between heavy and light chains

<400> SEQUENCE: 19

Gly Gly Gly Ser Gly Gly Gly Gly
  1               5

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence:synthetic
      biotinylation acceptor sequence and peptide linker
```

```
<400> SEQUENCE: 20

Gly Ser Thr Ser Gly Ser Gly Leu Asn Asp Ile Phe Glu Ala Gln Lys
 1               5                  10                  15

Ile Glu Trp His Glu
            20

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence:synthetic
      biotinylation acceptor sequence, peptide linker
      and hexa-histidine tag

<400> SEQUENCE: 21

Gly Ser Thr Ser Gly Ser Gly Leu Asn Asp Ile Phe Glu Ala Gln Lys
 1               5                  10                  15

Ile Glu Trp His Glu His His His His His His
            20                  25

<210> SEQ ID NO 22
<211> LENGTH: 29
<212> TYPE: PRT
<213> ORGANISM: Artificial Sequence
<220> FEATURE:
<223> OTHER INFORMATION: Description of Artificial Sequence:synthetic
      biotinylation acceptor sequence, peptide linker
      and hexa-histidine tag

<400> SEQUENCE: 22

Gly Ser Thr Ser His His His His His His Gly Ala Ala Gly Gly Leu
 1               5                  10                  15

Asn Asp Ile Phe Glu Ala Gln Lys Ile Glu Trp His Glu
            20                  25

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence:synthetic
      peptide linker and hexa-histidine tag

<400> SEQUENCE: 23

Gly Ser Thr Ser His His His His His His Gly Ala Ala Gly
 1               5                  10

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:synthetic
      hexa-histidine tag, 6xHis tag

<400> SEQUENCE: 24

His His His His His His
 1               5
```